United States Patent [19]

Simon et al.

[11] Patent Number: 5,725,554
[45] Date of Patent: Mar. 10, 1998

[54] SURGICAL STAPLE AND STAPLER

[75] Inventors: Denise M. Simon, Richland; Randall J. Hoyt, Kalamazoo, both of Mich.

[73] Assignee: Richard-Allan Medical Industries, Inc., Richland, Mich.

[21] Appl. No.: 134,555

[22] Filed: Oct. 8, 1993

[51] Int. Cl.$^6$ ................................ A61B 17/04
[52] U.S. Cl. ................................ 606/219; 227/19
[58] Field of Search ............... 606/220; 227/19; 411/457

[56] References Cited

U.S. PATENT DOCUMENTS

| | | | |
|---|---|---|---|
| 4,375,866 | 3/1983 | Giersch et al. | 227/19 |
| 4,477,008 | 10/1984 | Struble | 227/19 |
| 4,489,875 | 12/1984 | Crawford et al. | 227/19 |
| 4,523,695 | 6/1985 | Braun et al. | 227/19 |
| 4,747,531 | 5/1988 | Brinkehoff et al. | 227/19 |
| 4,802,478 | 2/1989 | Powell | 606/138 |
| 4,874,122 | 10/1989 | Froelich et al. | 227/19 |
| 4,899,745 | 2/1990 | Laboureau et al. | 411/457 |

*Primary Examiner*—Michael Buiz
*Attorney, Agent, or Firm*—Howard & Howard

[57] ABSTRACT

A surgical staple and stapler for use in stapling together the tissue of a patient. The staple is a rounded M-shape or gull wing shape in form. The surgical staple has a base which is bent downward in the center while the legs of the staple at each end of the base are outwardly bent. The outwardly bent legs of the staple are cut or formed to a sharp points at the end of the legs. The staple is circular in cross-section, but has a flat surface on the lower side. This staple facilitates stacking, feeding and removal of the staple. It further ensures a clean puncturing of the tissue that is stapled when used with the surgical stapling instrument.

7 Claims, 10 Drawing Sheets

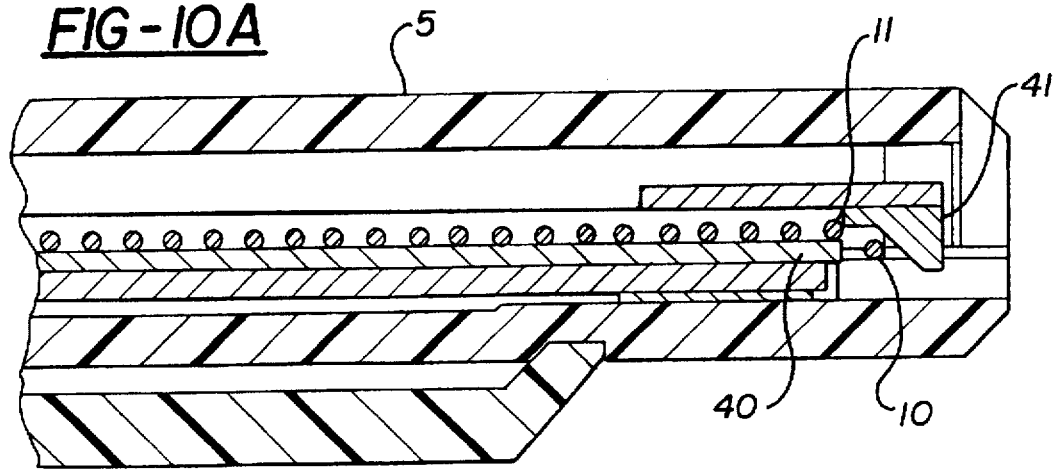
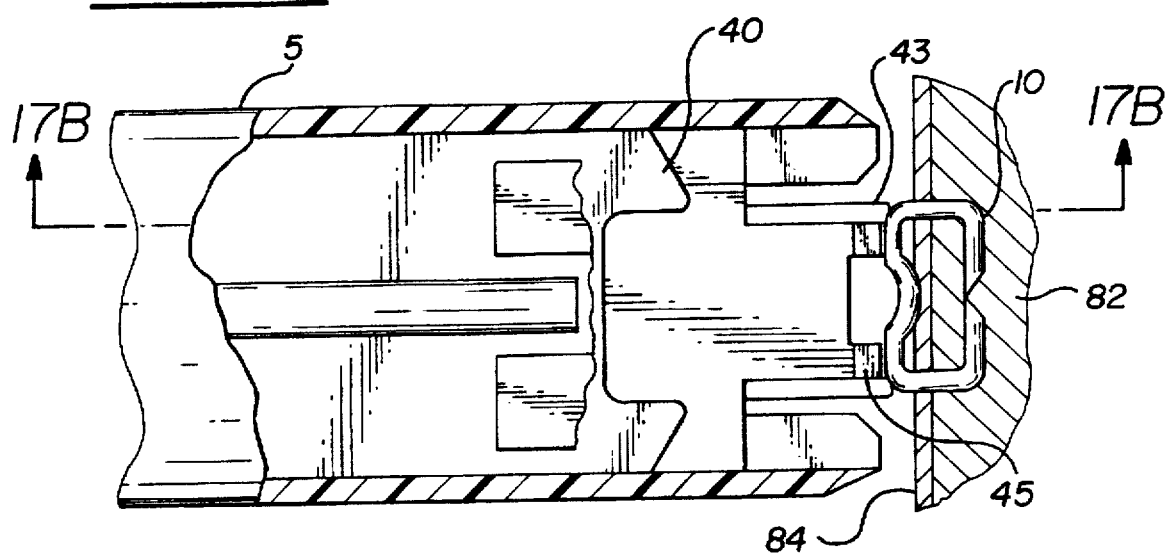

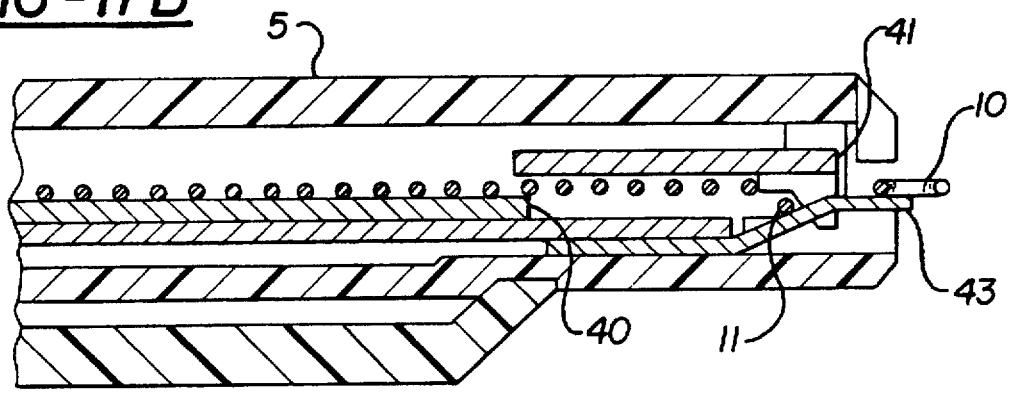
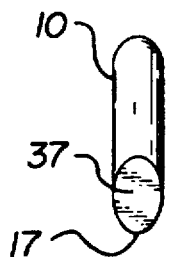
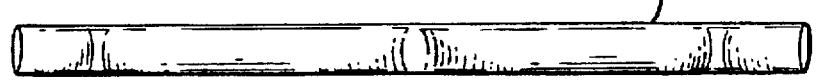

SURGICAL STAPLE AND STAPLER

FIELD OF THE INVENTION

The present invention relates generally to surgical staples and more specifically concerns surgical staples for use in internal or external surgical stapler instruments to close wounds or incisions in the body tissue of a patient.

BACKGROUND OF THE INVENTION

The surgical stapler instrument is a common medical instrument which is used to perform various functions such as closing internal wounds and suturing skin. Closing wounds and incisions by stapling is generally much easier and faster than stitching or suturing. The time savings may lessen the burden on the surgical team, may ease the trauma of the patient, and may reduce the expense of the surgical procedure. Furthermore, stitching is unsuitable for certain internal surgical procedures, such as endoscopic surgery.

Generally, a surgical stapling instrument will hold a series of staples in a stack. When the stapler is fired, the former moves forward and presses a staple against and around the rigid anvil. As the shape of the staple is changed to the closed position, points on the legs of the staple puncture tissue on opposite sides of a wound or incision and pull the tissue together. The surgical staple will maintain this closed position while the tissue heals. After healing, the staple may be removed or left permanently in place.

The staples used in surgical procedures have typically been inverted U-shaped staples similar in configuration to the kind used in paper staplers. Obviously, the stapling of human tissue is much more delicate than the stapling of paper. The conventional U-shaped staple does not feed easily when the staples are stacked in an end-to-end orientation, i.e. when the legs are in contact with the cross member, and is consequently susceptible to jamming in the stapler. Jamming of the staples in the stapler is annoying but tolerable when dealing with paper. However, jamming of the staple is much less tolerable during a surgical procedure when time is of the essence.

Furthermore, space is generally an important consideration in surgical instruments, particularly those used internally in endoscopic surgery. However, the conventional U-shaped staple is incapable of tight stacking in an end-to-end orientation. In addition, after the skin has healed, the staple should not cause any damage to the newly healed skin upon removal. Consequently, the staple must be easily removable.

SUMMARY OF THE INVENTION

The present invention overcomes the aforementioned problems through the use of a curved, open M-shaped or gull wing staple and a specially designed surgical stapler instrument.

It is the primary aim of the present invention to provide a staple that allows dense stacking with other staples without affecting the ability to fire the staples. Providing ease in feeding of the staples is another important objective of this invention. Consequently, it is also an object of this invention to reduce the frequency of jamming incidences.

Furthermore, it is an object to provide a staple that is rigid but readily deformable. A related object is to provide consistency in the final form of the staple. In addition, facilitating accurate positioning of the staple during firing is another object.

An additional object is to provide a staple and stapling mechanism which can be used in external applications, such as a skin stapler, and in internal applications, such as laparoscopic or endoscopic procedures.

Another object is to provide a staple which improves removal of the staple after healing. It is a further object of the invention to provide a staple which minimizes trauma to the tissue. Accordingly, it is an aim that the sharp edges cleanly penetrate the tissue without tearing.

A further object is to provide more accurate staple positioning by improving the visibility of the unformed staple.

An additional object is to provide a more consistent and final form of the staple by centering the staple on the two prongs of the anvil.

Other objects and advantages of the present invention and its details of construction will be apparent from a consideration of the following specification and accompanying drawings.

BRIEF DESCRIPTION OF THE DRAWINGS

FIG. 10A is a cross-sectional view of the cartridge in FIG. 9 taken along line 10A—10A;

FIG. 17A is a fragmentary top view after the mechanism has returned to its original positions;

FIG. 17B is a partial, cross-sectional view of FIG. 17A taken along line 17B—17B;

FIG. 19 is a top view of the staple in its original, unformed position;

FIG. 20 is a side view of the staple in its original, unformed position;

FIG. 21 is a bottom view of the staple in its original, unformed position.

While the invention will be described in connection with certain preferred embodiments, it is not intended to limit the invention to those embodiments. On the contrary, it is intended to cover all alternatives, modifications and equivalents as may be included within the spirit and scope of the invention.

DETAILED DESCRIPTION OF THE PREFERRED EMBODIMENT

Figure 1:
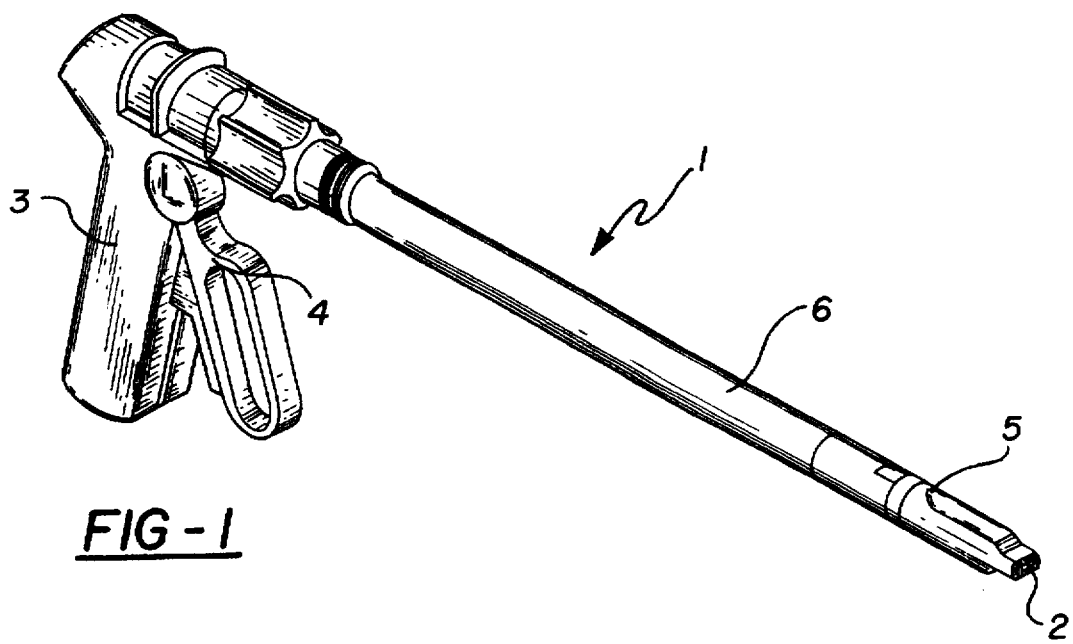
FIG. 1 is a right, front perspective view of the assembled stapling apparatus.

Turning now to the drawings, FIG. 1 shows one example of an endoscopic surgical stapler. Generally speaking, an endoscopic stapler 1 includes a long endoscopic arm 6, a stapling actuation mechanism 2 located at the end of the endoscopic arm 6 and within the distal cartridge 5, a handle area 3 with a trigger 4. The trigger 4 is the control mechanism operated by the surgeon. The operation of the trigger 4 causes a linear force to travel through the length of the arm 6 to the stapling actuation mechanism 2. This linear force activates the stapler actuation mechanism 2.

Figure 2:
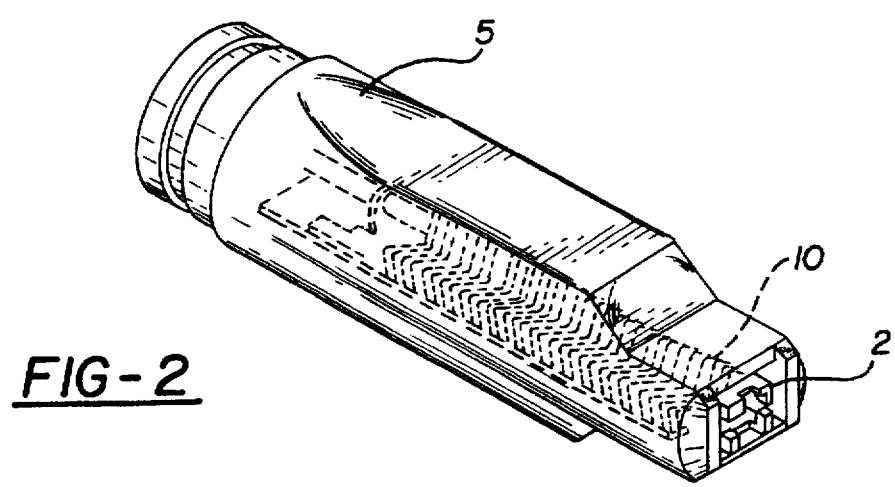
FIG. 2 is an enlarged, perspective view of the cartridge containing the stapling mechanism and loaded with a stack of staples.
Figure 3:
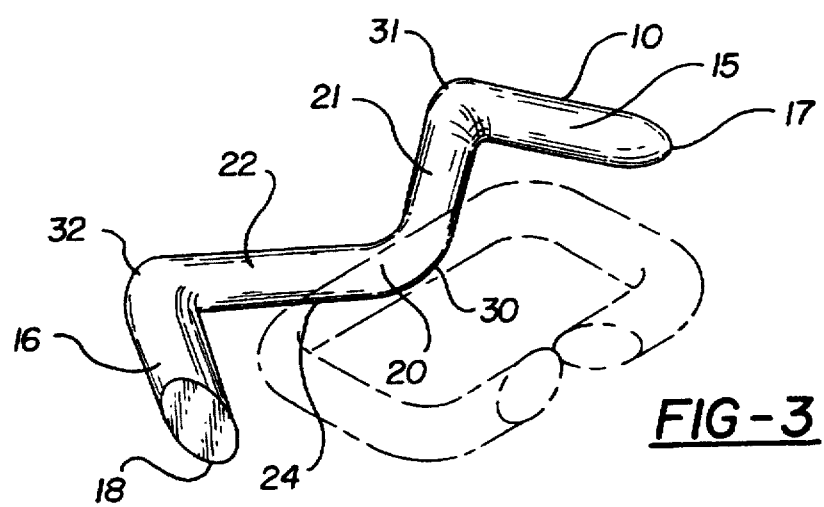
FIG. 3 is perspective view of the staple in its original position and the formed position is shown in broken lines.

FIG. 2 is a perspective view of the cartridge 5 containing the stapling actuation mechanism 2. A stack of staples 10 is loaded within the cartridge 5. As shown in FIG. 3 which is the perspective view of the preferred embodiment of the staple invention and the front view in FIG. 4, the staple 10 is basically M-shaped or gull wing shaped. However, at the bends 30, 31, and 32, the staple 10 is curved rather than sharply bent.

The base 20 is bent downward in the center to form symmetrical right and left portions 21 and 22. The right and left portions 21 and 22 of the base 20 are at a 30 degree angle from horizontal. Furthermore, the base terminates with legs 15 and 16 which are bent ninety degrees (90°) to right and left portions 21, 22. More specifically,, the right portion 21 of the base is at a right angle with the right leg 15 and the left portion 22 of the base is at a right angle with the left leg 16. The openness of the staple 10 and roundness of the bends 30, 31 and 32 facilitate tight stacking without creating undesirable clinging between staples.

Figure 4:
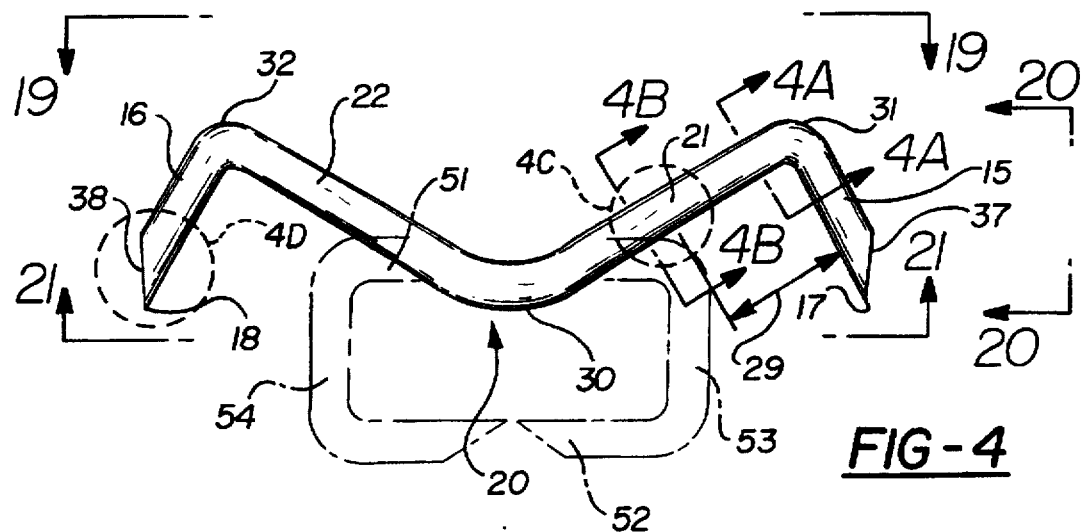
FIG. 4 is a front view of the staple in its original position and the formed position is shown in broken lines.
Figure 4A:
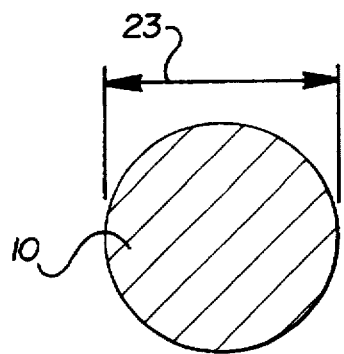
FIG. 4A is an enlarged cross-sectional view of the staple taken along line 4A—4A of FIG. 4.
Figure 4B:
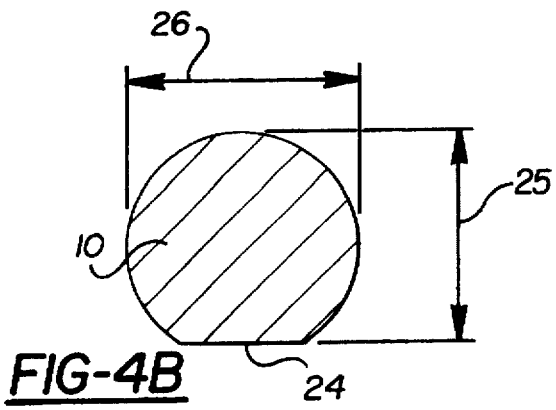
FIG. 4B is an enlarged cross-sectional view of the staple taken along line 4B—4B of FIG. 4.
Figure 4C:
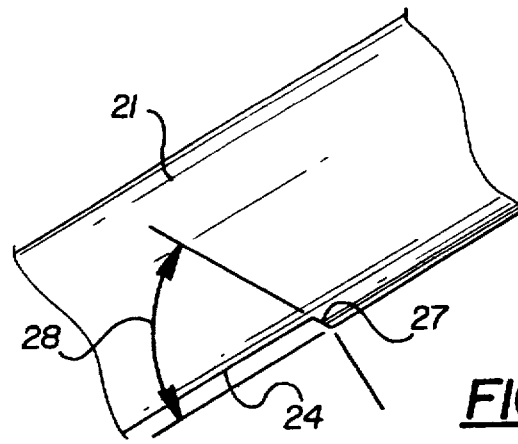
FIG. 4C is an enlarged partial view of the staple at detail area 4C of FIG. 4.

Although modifications may be made without departing from the spirit of this invention, the staple 10 of this embodiment is formed of a circular titanium wire as shown in FIG. 4A. The diameter 23 of the wire is approximately 0.022 inches. However, in one embodiment, the right and left portions 21,22 have a flat surface 24 as shown in FIG. 4B. The distance 25 between the flat surface 24 and the upper surface of the staple is approximately 0.02 inches and the maximum swelling of the distance 26 is approximately 0.023 inches. The flat surface 24 extends along the bottom of each right and left portion 21,22 and begins at a distance 29 of approximately 0.084 inches from each leg 15,16. As shown in FIG. 4C, a beveled surface 27 transitions the circular surface of the staple 10 to the flat surface 24. The beveled surface 27 is at an angle 28 of approximately sixty degrees (60°) from the circular surface of the staple 10. As will be described later, the purpose of the flat surface 24 and the beveled surface 27 is to properly engage the anvil and to uniformly form the staple 10.

Each leg 15 and 16 is approximately one quarter the length of the base 20. In this preferred embodiment, the legs 15 and 16 are both approximately 0.09 inches in length, while the right and left portions 21 and 22 of the base 20 are each approximately 0.13 inches in length. Other lengths may be substituted if the proportions are roughly equivalent.

The proportions and angles of the staple are important because, in the formation process, the staple 10 becomes rectangular in shape, as seen in FIGS. 3 and 4 in broken lines. As shown in FIGS. 3 and 4, during the staple formation process pressure is applied approximately midway in the right and left portions 21 and 22 of the base 20 which causes the base 20 to be straightened and then bent. Ultimately, the base 20 forms the upper horizontal side 51 and the two vertical sides 53 and 54 of the box. When the base 20 is bent, the legs 15 and 16 meet to form the lower horizontal side 52 of the box.

Figure 5:
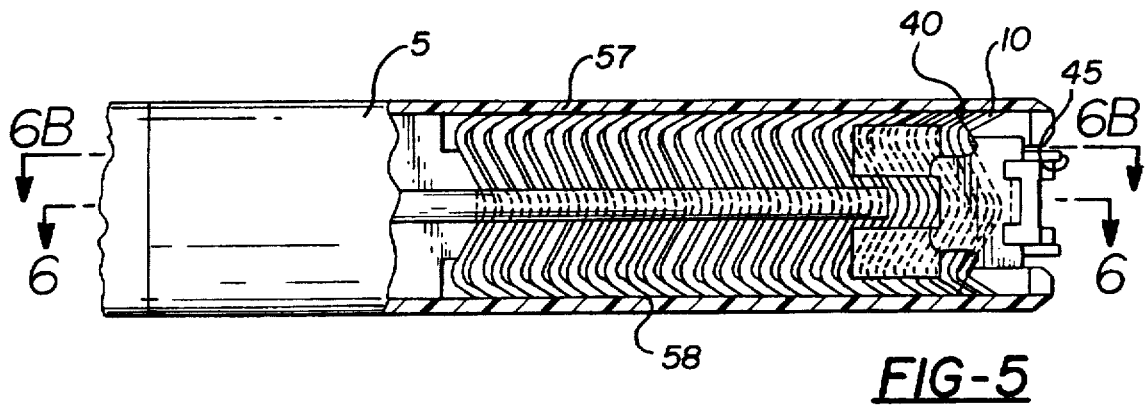
FIG. 5 is a fragmentary top view of the cartridge with the staples loaded and ready for the initial firing process.
Figure 6:
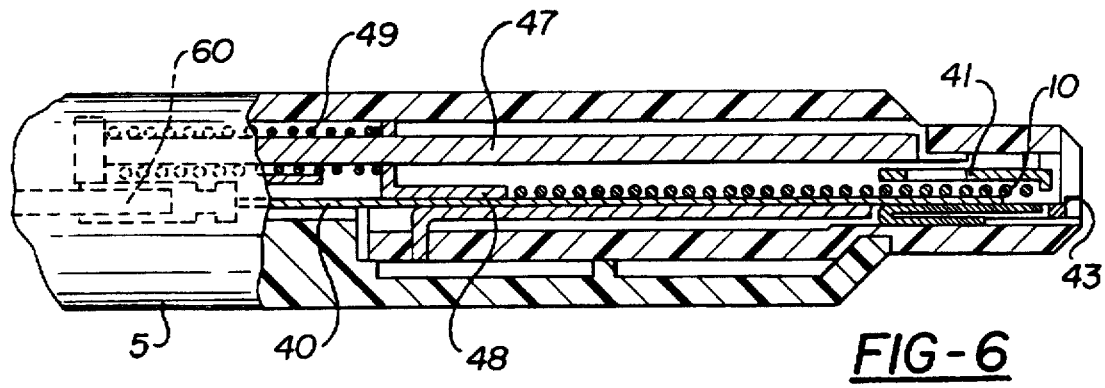
FIG. 6 is a fragmentary, cross-sectional view of the cartridge taken along line 6—6 in FIG. 5.
Figure 4D:
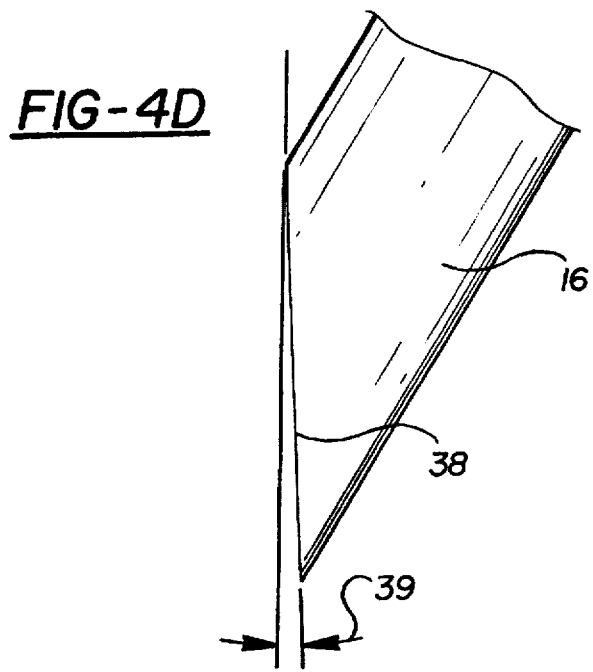
FIG. 4D is an enlarged partial view of the staple at detail area 4D of FIG. 4.

The legs 15 and 16 of the staple 10 have sharp points 17 and 18 to puncture body tissue. These points 17 and 18 are created such that the outwardly bent legs 15 and 16 have almost vertical edges 37 and 38. As shown in FIG. 4D which is an enlarged view of the edge 38 of leg 16, the edge 38 is at an angle 39 from the vertical. In this particular embodiment, the angle 39 is approximately three degrees (3°) from the vertical. The angle 39 prevents the edges 37, 38 from jamming into the inner walls 57, 58 of the cartridge 5. However, the angle 39 could be between zero degrees (0°) and thirty degrees (30°). When stacked in the stapler, these edges 37 and 38 on the legs 15 and 16 allow the staple 10 to slide easily within the cartridge 5 upon the inner walls 57 and 58 which are molded in the cartridge 5 as illustrated in FIG. 5. As shown in FIGS. 5 and 6, the staples lay flat in a tandem or sequential row such that the upperside of the legs 15,16 of one staple abuts the underside of the legs 15,16 of the staple directly behind it. As shown in FIGS. 5 and 6, the stack of staples lies directly upon the former 40 between the inner walls 57 and 58 of the cartridge 5.

This formation process occurs after the stapler instrument 1 is initially fired. In FIGS. 5 and 6, the stack of staples 10 is shown in an initial loaded position within the cartridge 5. After initial loading of a stack of staples 10, the stapler 1 must be initially fired to place the staples in position for ejection, i.e., the initial firing will not eject a staple. Thus, a measure of safety against unwanted staple firing is provided.

Figure 6A:
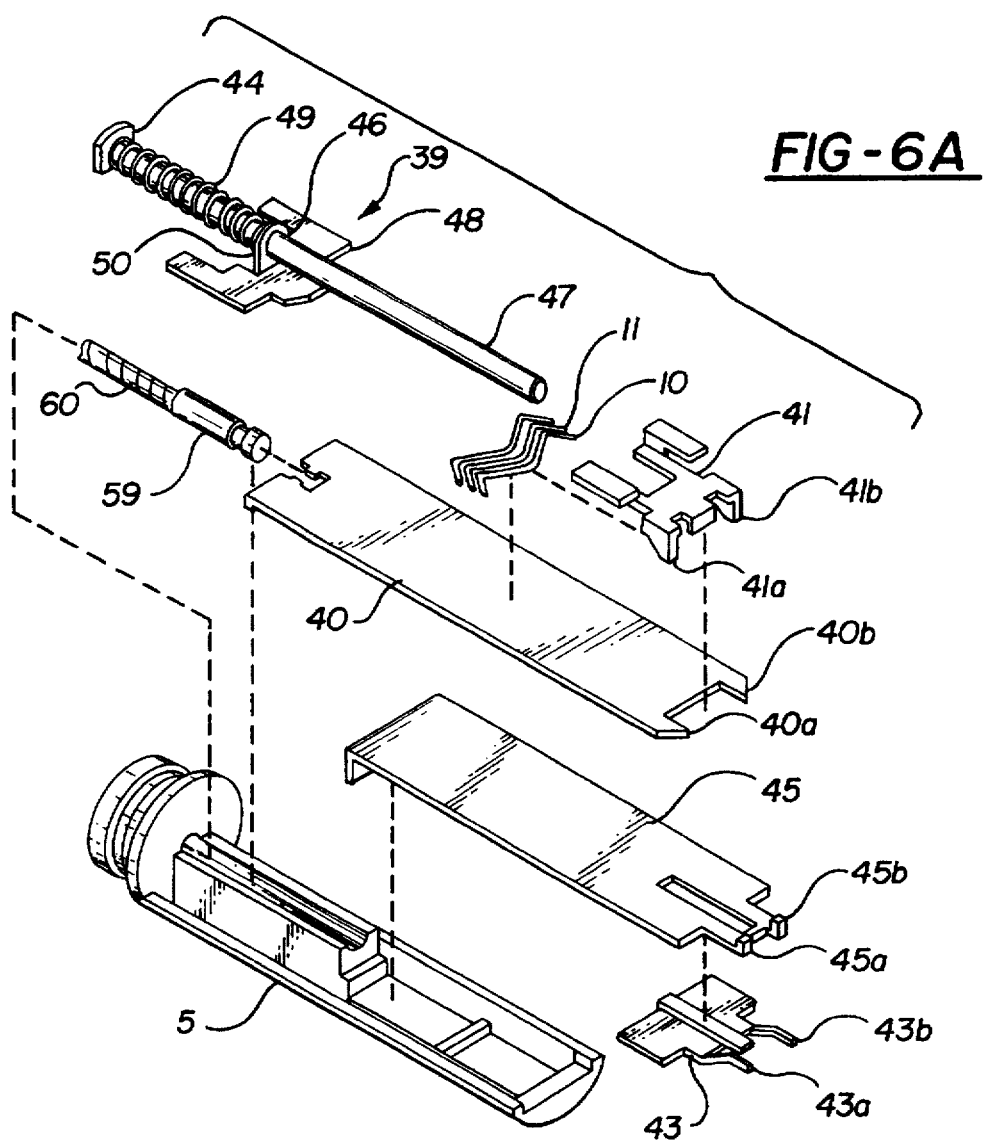
FIG. 6A is a partial, exploded view of the cartridge.

In FIGS. 5, 6 and 6A, the various parts of the stapling actuation mechanism 2 are illustrated. The actuation mechanism 2 includes the former 40, the staple stop 41, the anvil 45, the spring support 47, the staple pusher 48, the spring 49, the cable connector 59 and the driver 60. The former 40, the staple stop 41, the staple lifter 43 and the anvil 45 each terminate into two symmetrical prongs, respectively a and b, which react with opposite sides of the staple 10 at predetermined points.

Figure 7:
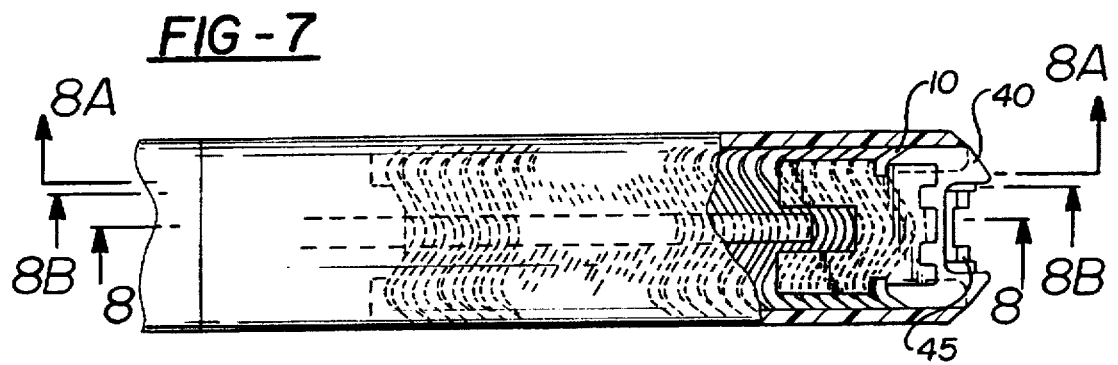
FIG. 7 is a fragmentary, cross-sectional top view of the cartridge at an intermediate stage in the initial firing process.
Figure 6B:
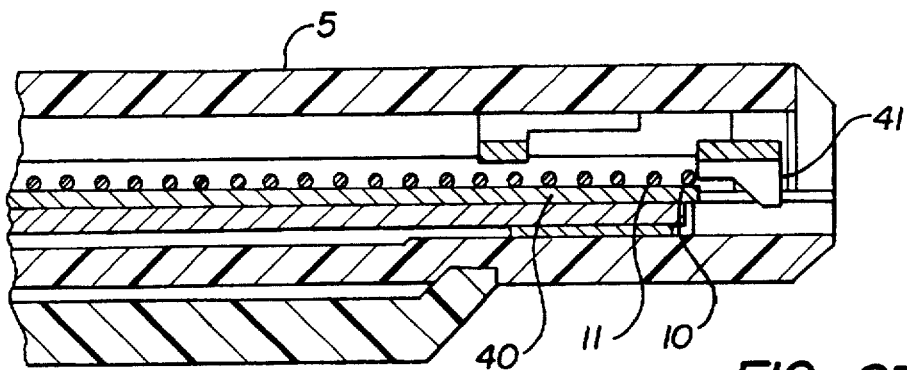
FIG. 6B is a partial, cross-sectional view of the cartridge taken along line 6B—6B in FIG. 5.
Figure 8A:
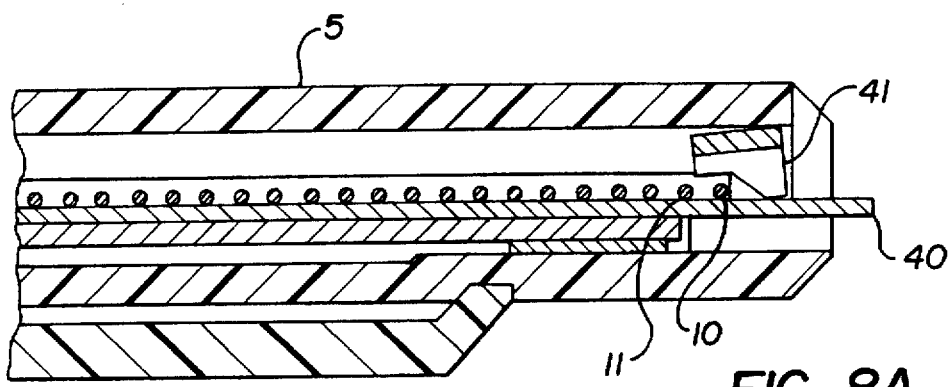
FIG. 8A is a cross-sectional view of the cartridge in FIG. 7 taken along line 8A—8A.
Figure 8B:
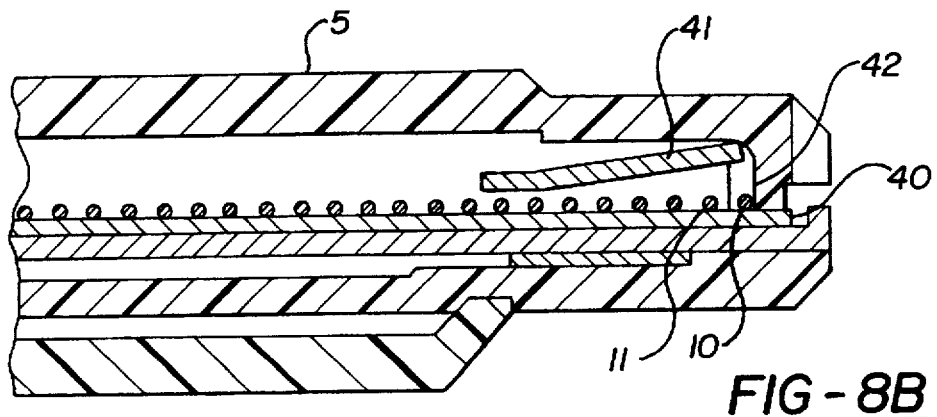
FIG. 8B is a cross-sectional view of the cartridge in FIG. 7 taken along line 8B—8B.
Figure 8:
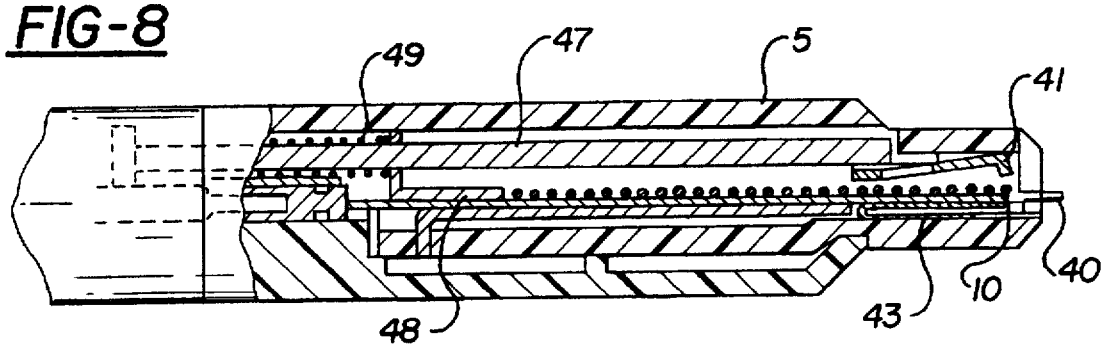
FIG. 8 is a cross-sectional view of the cartridge in FIG. 7 taken along line 8—8.

Referring now to FIGS. 6A, 7 and 8, an actuation of the stapler mechanism 2 occurs when a linear force is provided from the stapler 1 to the stapler cartridge 5 via a driver 60. The driver 60 is connected to the former 40 by connector 59 and the driver 60 causes the former 40 to move forward. As the former 40 moves forward, the former contacts the legs 41a, 41b on the staple stop 41 causing it to pivot upward, as seen in FIG. 8A.

The stack of staples 10 will move forward due to pressure from the forward biasing assembly 39 until the forwardmost staple 10 comes into contact with the cartridge stops 42, shown in FIG. 8B, which depend downward from the upper half of the cartridge 5. In the preferred embodiment, as best seen in FIG. 6A, the forward biasing assembly 39 consists of the staple pusher 48 located above the former 40 and behind the staple stack 10, a spring 49, and a spring support 47. The spring 49 is designed to slide upon the elongated, cylindrical support 47 which has one enlarged end 44 to engage the spring 49. The staple pusher 48 has an integral vertical flange 50 with a hole 46 which slides onto the spring support 47. Consequently, the spring 49 biases the staple pusher 48 forward. In turn, because the last staple of the stack lies directly in front of the pusher 48, the staple pusher 48 advances the stack of staples 10.

Figure 9:
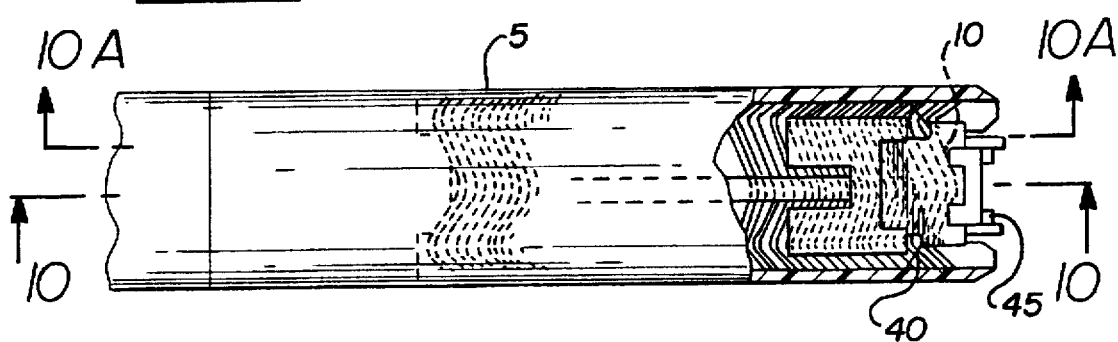
FIG. 9 is a fragmentary top view of the cartridge with the staples loaded and ready for ejection firing.
Figure 10:
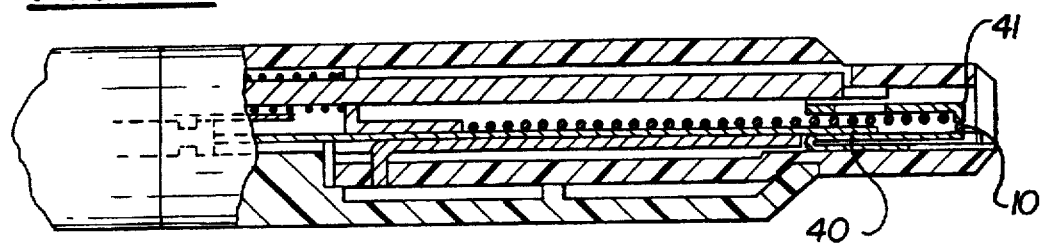
FIG. 10 is a cross-sectional view of the cartridge in FIG. 9 taken along line 10—10.
Figure 11:
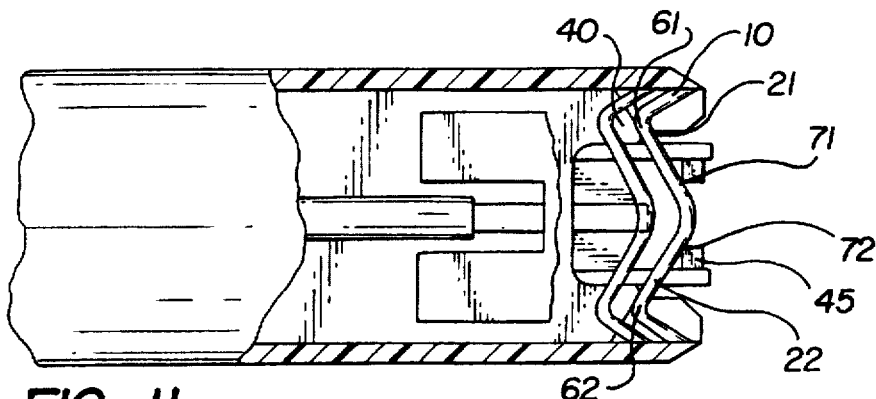
FIG. 11 is a fragmentary top view of the cartridge at an early stage in the staple formation process.

Turning now to FIGS. 9, 10 and 10A, when the former 40 travels back to the starting position, the staple stop 41 resumes its previous position. Because the first staple 10 is directly below the staple stop 41 at the point in the firing process illustrated in FIG. 8, the first staple 10 is pushed downward in front of the retracting former 40. This is best seen in FIG. 10A. The stapler 1 is now ready for firing the staple 10. When the actuation mechanism 2 is triggered with the staples in the ready position, the former 40 again will move forward. As the former 40 moves forward, the former 40 pushes the staple 10 which is in front of the former 40. It should be noted that the contact between the prongs of the former 40 with the V-shaped base 20 of staple 10 provides lateral stability and hence, there is no lateral shifting of the staple 10. Furthermore, self-centering of the staple 10 is produced by this contact. As can be seen in FIG. 11, the staple 10 will cease its forward movement when it contacts the anvil 45. When the staple 10 comes into contact with the split anvil 45 or anvil prongs 45a, 45b, the anvil provides centering of the staple for a more uniform shape. More specifically, the staple is accurately positioned on the anvil so that the right and left portions 21, 22 of the base 20 are equally positioned on the anvil 45 in order to uniformly bend these portions around the anvil and create a uniform shape. The flat configuration of the anvil contacting the flat surface 24 of the staple 10 prevents rotation by the staple and consequently, there is no unwanted rotation of the staple during formation of the staple.

Because the former 40 will continue to move forward, it exerts pressure on the staple 10 at two points 61 and 62 on the base of the staple 10. One pressure point on each the right and left portions 21 and 22 of the base 20 is located immediately adjacent on the outside of the stopping pressure points 71 and 72 supplied by the anvil 45 on the opposite side of the staple 10. The forward pressure by the former 40 at points 61 and 62 resisted by the stopping pressure of the anvil 45 at points 71 and 72 causes the staple 10 to bend.

Figure 12:
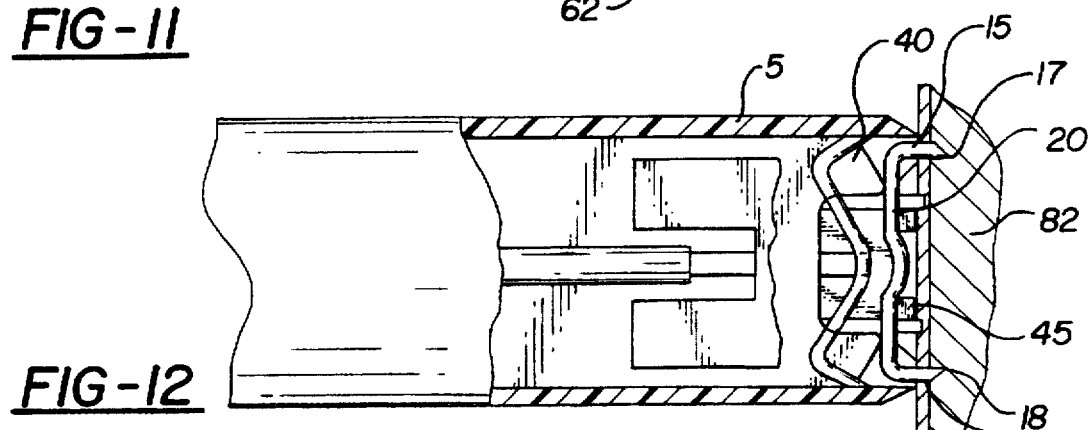
FIG. 12 is a fragmentary top view of the cartridge at a secondary stage in the staple formation process.
Figure 13:
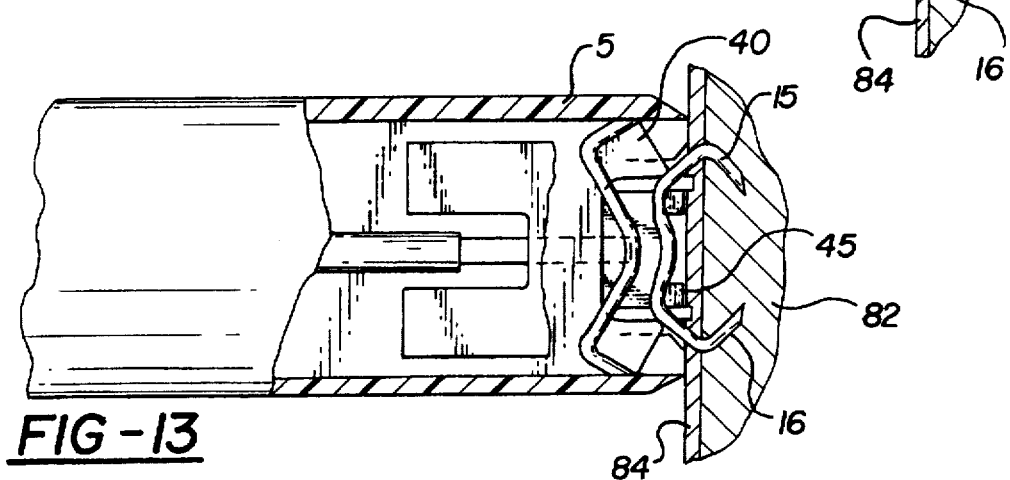
FIG. 13 is a fragmentary top view at a tertiary stage in the staple formation process.
Figure 14:
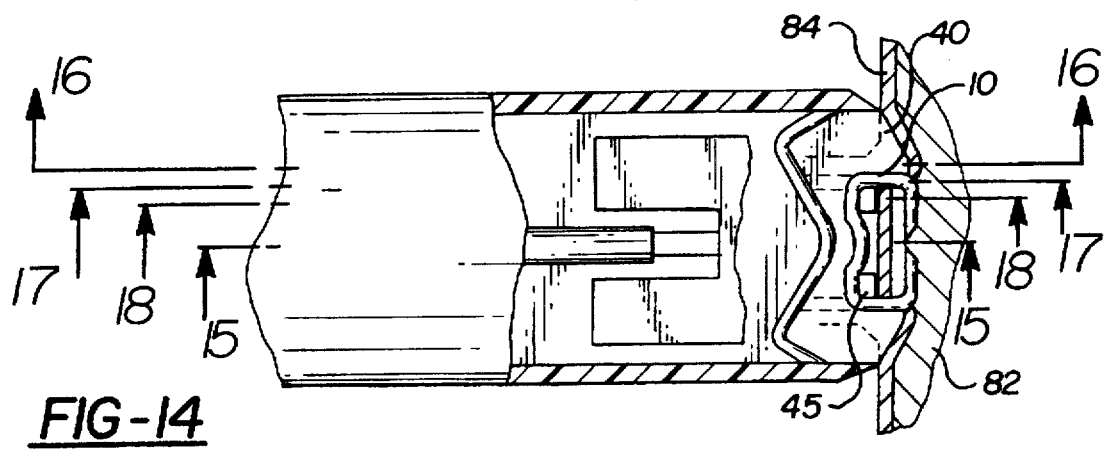
FIG. 14 is a fragmentary top view at the final stage in the staple formation process, just before the mechanism returns to its original positions.

As the staple 10 is bending, as shown in FIG. 12, the base 20 straightens and the legs 15 and 16 move out of the cartridge 5. At this time, the sharp points 17 and 18 on each of the staple legs 15 and 16 will pierce tissue 82 on opposite sides of the wound or incision. In addition, the stapler could also be used in conjunction with mesh 84. FIG. 13 shows the staple 10 at a later stage in the bending. At this point, the staple 10 will be pulling the tissue closer together. Finally, at the point shown in FIG. 14, the forming of the staple 10 is complete. The staple 10 is in its rectangular, final form and the tissue should be held tightly together.

Figure 17:
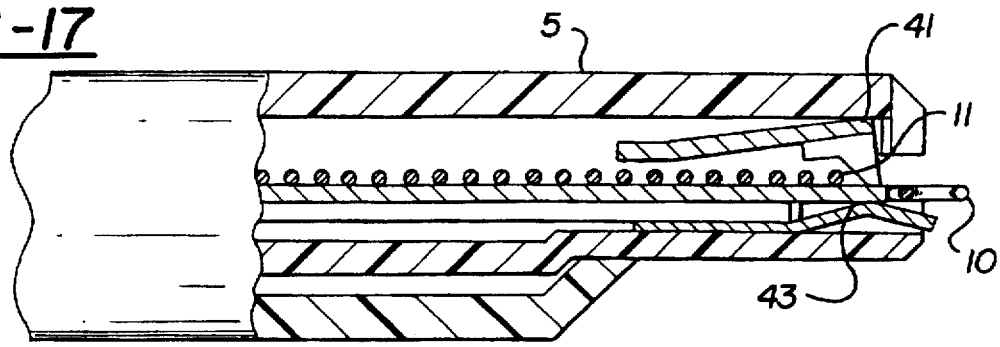
FIG. 17 is a partial, cross-sectional view of FIG. 14 taken along line 17—17.

Once the formation process is finished, the former 40 moves back to the starting position. While the former 40 was moving forward, it deflected the staple lifter 43 downward and had pivoted the staple stop 41 upward as shown in FIG. 17. As the former 40 returns to its starting position, the staple lifter 43 and staple stop 41 will resume their default positions. As the staple lifter 43 moves upward from its deflected position in FIG. 17 to its default position in FIG. 17B, the formed staple 10 is lifted over the anvil 45 so that the stapler instrument 1 can be moved away from the tissue 82 or mesh 84 which is now connected by the formed staple 10.

Figure 15:
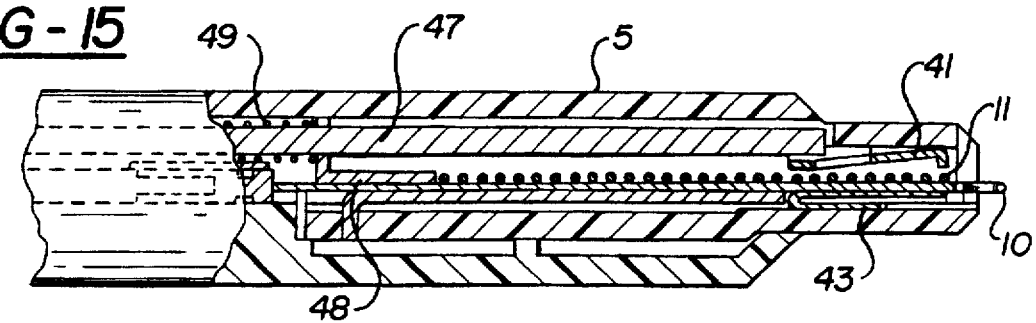
FIG. 15 is a partial, cross-sectional view of FIG. 14 taken along line 15—15.
Figure 16:
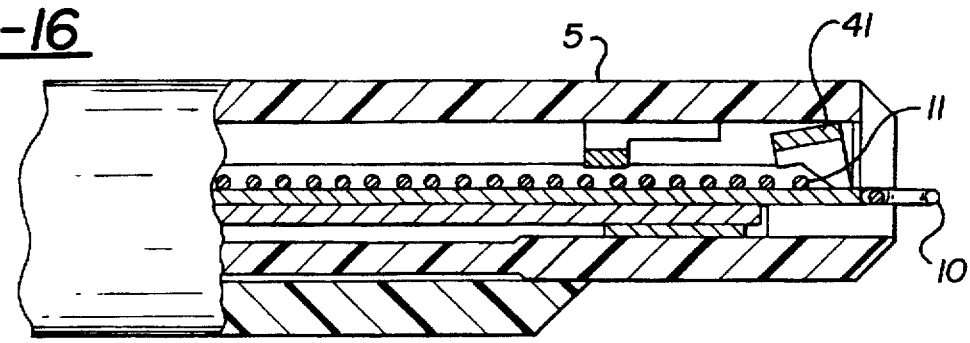
FIG. 16 is a partial, cross-sectional view of FIG. 14 taken along line 16—16.
Figure 18:
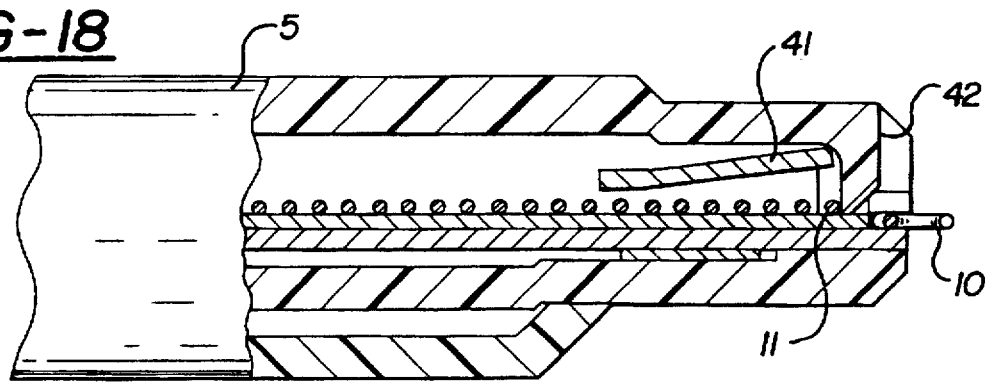
FIG. 18 is a partial, cross-sectional view of FIG. 14 taken along line 18—18.

Furthermore, because the staple stop 41 had been pivoted upward, as shown in FIGS. 15 and 16, the staple pusher 48 had pushed the stack of staples 10 forward. Again, as shown in FIG. 18, the cartridge stops 42 prevent the stack of staples 10 from moving forward when the next succeeding staple 11 contacts the cartridge stop 42. When former 40 moves back and the staple stop 41 pivots downward, another staple 11 is placed in front of the former 40 as shown in FIG. 10A. The stapler 1 is ready for firing a second staple 11 into the tissue.

After the requisite number of staples have been introduced into the tissue to staple the tissue together, the staples 10, 11, et. al. remain in the tissue during healing. After healing, the surgical staples can be easily removed because the staple centers the staple remover. More specifically, the center portion of the staple remover will center on the staple center bend 30. Thus, as the staple remover is utilized, the right and left portions 21, 22 of the staple bend upwards uniformly and substantially equally. Consequently, the substantially equal bending of the staple allows the staple to be removed without damaging the surrounding tissue. Alternatively, the staple can be formed of biologically inert metal, such as titanium or stainless steel, and remain permanently in the body. In another alternative embodiment, the staple is made of a biologically absorbable material, such as modified polymer.

Although an endoscopic stapler is shown in FIG. 1, this staple and stapler mechanism can also be used for external stapling, such as skin staplers.

Therefore as disclosed above, this invention satisfies the objects and advantages noted above. More specifically, as can be seen from this invention, the shape of the staple facilitates the feeding of staples. Furthermore, when the staples are stacked in an end-to-end orientation, this staple is less susceptible to jamming. In addition, due to the configuration of the anvil and the shape of the staple, the staple centers on the anvil and improves the consistency of the final form of the staple. Also, due to the configuration of the former and the shape of the staple, the former centers the staple and improves the consistency of the final form of the staple.

What is claimed is:

1. A surgical stapler for closing staples to join incised tissue comprising: a staple, wherein said staple comprises;
   a staple base having symmetric right and left portions joined at one central bend portion;
   a right leg and a left leg extending from said right and left portions, each of said legs having a proximal end and a distal end, wherein said proximal end of said right leg joins said right portion at a right upper bend and said proximal end of said left leg joins said left portion at a left upper bend;

an anvil for supporting said staple base as said staple is closed; and a former having two prongs separated by a gap for closing or forming said staple around said anvil;

wherein said former has surfaces which correspond to and bear on said right and left portions for centering said staple on said anvil prior to closing said staple.

2. A surgical stapler according to claim 1, wherein said central bend portion has a bend angle of about 120°.

3. A surgical stapler according to claim 1, wherein said right upper bend and said left upper bend each have a bend angle of about 90°.

4. A surgical stapler according to claim 1, wherein said prongs contact said right and left portions.

5. A surgical stapler according to claim 1, wherein said staple is generally circular in cross-section but includes a flat portion on the underside of said staple.

6. A surgical stapler for closing staples to join incised tissue comprising: a staple, wherein said staple comprises;

a staple base having symmetric right and left portions joined at one central bend portion;

a right leg and a left leg extending from said right and left portions, each of said legs having a proximal end and a distal end, wherein said proximal end of said right leg joins said right portion at a fight upper bend and said proximal end of said left leg joins said left portion at a left upper bend;

an anvil for supporting said staple base as said staple is closed; and a former for closing or forming said staple around said anvil maintains said central bend portion;

wherein said former has surfaces which correspond to and bear on said right and left portions for centering said staple on said anvil prior to closing said staple.

7. A surgical staple according to claim 6, wherein said central bend portion maintains an angle of about 120°.

* * * * *